(12) United States Patent
Unluhisarcikli et al.

(10) Patent No.: US 9,198,821 B2
(45) Date of Patent: Dec. 1, 2015

(54) LOWER EXTREMITY EXOSKELETON FOR GAIT RETRAINING

(71) Applicants: Northeastern University, Boston, MA (US); Spaulding Rehabilitation Hospital Corporation, Boston, MA (US)

(72) Inventors: Ozer Unluhisarcikli, Allston, MA (US); Constantinos Mavroidis, Arlington, MA (US); Paolo Bonato, Somerville, MA (US); Maciej Pietrusisnki, Cambridge, MA (US); Brian Weinberg, San Diego, CA (US)

(73) Assignees: NORTHEASTERN UNIVERSITY, Boston, MA (US); SPAULDING REHABILITATION HOSPITAL CORPORATION, Boston, MA (US)

( * ) Notice: Subject to any disclaimer, the term of this patent is extended or adjusted under 35 U.S.C. 154(b) by 627 days.

(21) Appl. No.: 13/631,322

(22) Filed: Sep. 28, 2012

(65) Prior Publication Data
US 2013/0226048 A1 Aug. 29, 2013

Related U.S. Application Data

(60) Provisional application No. 61/540,178, filed on Sep. 28, 2011.

(51) Int. Cl.
*A61H 1/00* (2006.01)
*A61F 5/00* (2006.01)
(Continued)

(52) U.S. Cl.
CPC .. *A61H 1/00* (2013.01); *A61F 5/01* (2013.01); *A61H 1/024* (2013.01); *A61H 1/0244* (2013.01);
(Continued)

(58) Field of Classification Search
CPC ........................ A63B 23/035–23/0405; A63B 23/0417–23/0429; A63B 23/0458–23/10; A63B 2023/0411; A63B 2023/0441–2023/0452; A63B 2220/16; A61F 2/60–2/605; A61F 2/2164–2/646; A61F 2/66–2/6607; A61F 2/68; A61F 2/70; A61F 2/72; A61F 2/76; A61F 2/78; A61F 2/80; A61F 2/7812; A61F 2/843; A61F 2002/607–2002/608; A61F 2002/648; A61F 2002/6614–2002/6692; A61F 2002/6809–2002/689; A61F 2002/701–2002/708; A61F 2002/74–2002/748; A61F 2002/7605–2002/7695; A61F 2002/7806; A61F 2002/785–2002/7893; A61F 2002/802–2002/807; A61F 2002/30527; A61F 2002/30537–2002/30543; A61F 2002/3055–2002/30555; A61F 2002/30558–2002/3056; A61F 2002/30601; A61F 2002/30649–2002/30652; A61F 2002/502; A61F 2220/0025–2220/0041; A61F 2220/0091; A61F 2250/0065; A61F 5/01–5/0127; A61F 2005/0132–2005/0179; A61F 2005/0188; A61F 1/0262; A61G 3/00; A61H 2203/0406; A61H 2201/50; A61H 2201/5002; A61H 2201/5058; A61H 2201/5064; A61H 2201/5069; A61H 2201/5071

See application file for complete search history.

(56) References Cited

U.S. PATENT DOCUMENTS 5,282,460 A 2/1994 Boldt
2003/0093021 A1 5/2003 Goffer
(Continued)

OTHER PUBLICATIONS

Aoyagi, D. et al., "A Robot and Control Algorithm That Can Synchronously Assist in Naturalistic Motion During Body-Weight-Supported Gait Training Following Neurologic Injury," IEEE Transactions on Neural Systems and Rehabilitation Engineering, vol. 15, No. 3, pp. 387-400 (Sep. 2007).

(Continued)

*Primary Examiner* — Rachel Young
(74) *Attorney, Agent, or Firm* — Wilmer Cutler Pickering Hale and Dorr LLP

(57) ABSTRACT

The Active Knee Rehabilitation Orthotic System (ANdROS) is a wearable and portable assistive tool for gait rehabilitation and monitoring of people with motor control deficits due to a neurological ailment, such as stroke. ANdROS reinforces a desired gait pattern by continually applying a corrective torque around the knee joint, commanded by a impedance controller. A sensorized yet unactuated brace worn on the unimpaired leg is used to synchronize the playback of the desired trajectory based on the user's intent. The device is mechanically grounded through two ankle foot orthoses (AFOs) rigidly attached to the main structure, which helps reduce the weight perceived by the user.

15 Claims, 20 Drawing Sheets

(51) Int. Cl.
  *A61H 3/00* (2006.01)
  *A61H 1/02* (2006.01)
  *A61F 5/01* (2006.01)

(52) U.S. Cl.
  CPC .......... *A61H 3/00* (2013.01); *A61H 2201/1215* (2013.01); *A61H 2201/165* (2013.01); *A61H 2201/5007* (2013.01); *A61H 2201/5061* (2013.01); *A61H 2201/5069* (2013.01)

(56) References Cited

U.S. PATENT DOCUMENTS

| | | | |
|---|---|---|---|
| 2007/0010378 A1 | 1/2007 | Katoh et al. | |
| 2008/0097269 A1 | 4/2008 | Weinberg et al. | |
| 2008/0161937 A1* | 7/2008 | Sankai | 623/25 |
| 2011/0040216 A1* | 2/2011 | Herr et al. | 601/34 |
| 2011/0105966 A1* | 5/2011 | Kazerooni et al. | 601/35 |
| 2012/0283844 A1* | 11/2012 | Langlois | 623/24 |
| 2013/0197408 A1* | 8/2013 | Goldfarb et al. | 601/35 |

OTHER PUBLICATIONS

Hesse, S. et al., "A mechanized gait trainer for restoration of gait," Journal of Rehabilitation Research and Development, vol. 37, No. 6, pp. 701-708 (Nov./Dec. 2000).

International Search Report and Written Opinion issued by the International Searching Authority for Application No. PCT/US2012/058041 mailed on Dec. 24, 2012 (10 pages).

Patel, S. et al., "Effects on Normal Gait of a New Active Knee Orthosis for Hemiparetic Gait Retraining," Proceedings of the 28th IEEE EMBS Annual International Conference, New York City, USA, pp. 1232-1235 (Aug. 30-Sep. 3, 2006).

Weinberg, B. et al., "Design, Control and Human Testing of an Active Knee Rehabilitation Orthotic Device," IEEE International Conference on Robotics and Automation, Roma, Italy, pp. 4126-4133 (Apr. 10-14, 2007).

* cited by examiner

LOWER EXTREMITY EXOSKELETON FOR GAIT RETRAINING

CROSS-REFERENCE TO RELATED APPLICATIONS

This application claims the benefit of U.S. Provisional Patent Application No. 61/540,178, filed on Sep. 28, 2011, which is incorporated herein by reference.

BACKGROUND

1. Field of Invention

This invention generally relates to systems for gait retraining. More particularly, the invention relates to a lower extremity exoskeleton designed as a wearable and portable assistive tool for gait neuro-rehabilitation which targets primary gait deviations (e.g. knee hyperextension during stance and stiff-legged gait during swing phase) by reinforcing a desired gait pattern.

Gait can be defined as a person's particular manner of walking. The upright posture assumed during biped walking is unstable in its nature, and walking is oftentimes described as "a continuous forward fall". Of course, we actually (almost) never fall thanks to the sophisticated coordination of our limbs. Unfortunately, being such a complex process, gait is affected substantially by neurological impairments. According to a 2009 survey, 6.9% of the population in the United States reported an ambulatory disability. The ability to walk and the quality of life are strongly correlated, and therefore restoration of normal gait in the disabled population is of great importance.

2. Description of Related Art

Biomechanics of Walking

It is easy to underestimate the complexity of locomotion, since we walk automatically and with relative ease. Biped gait is a very intricate process that involves the cooperation of several subsystems. From a mechanical point of view, gait is achieved through the coordination of multiple appendages that are actuated by multiarticular muscles that span more than one joint. From a control system point of view, gait involves the dynamic interactions between the central nervous system (CNS) and the peripheral nervous system (PNS).

The human leg has more than seven major degrees of freedom (DoFs), actuated by more than fifteen muscle groups. The human hip is a ball and socket joint with 3-DoFs that allow motion in all three anatomical planes. The knee joint can be simplified as 1-DoF joint that moves along the sagittal plane. Its motions are simply defined as knee flexion/extension. The ankle displays dorsiflexion/plantarflexion in the sagittal plane and inversion/eversion in the coronal plane.

Walking is a quasi-cyclic motion, which can be divided into gait cycles defined as the period between successive heel strikes of the same foot. Generally, the beginning (and the end) of a gait cycle is defined with the ground contact of the same foot. The gait cycle can further be divided into phases and sub-phases. The stance phase is the period where the particular foot is on the ground and supports the body, which constitutes approximately 60% of the gait cycle. The swing phase is where the leg is carried forward, and covers the remaining 40%. In symmetrical gait, both limbs are in contact with the ground for about 10% of the cycle, which is referred to as double (limb) support. FIG. 1 shows the phases and sub-phases of gait.

The gait cycle is useful in studying gait patterns independently from the variations in timing, since it is defined by events rather than time. Variations in joint parameters throughout a complete gait cycle are typically represented by gait trajectories. Even though the gait cycle representation is normalized for time, the gait trajectories are actually influenced by variations in time dependent parameters, such as walking speed and cadence. FIG. 2 shows the mean trajectories of the angle, velocity, and power of the hip, knee, and ankle joints presented as a function of gait cycle (%). Trajectories are shown for six discrete walking velocities ranging from 1 km/hr to 6 km/hr.

Humans achieve energy-efficiency during gait by using gravity as the main driving force. There is a continuous exchange of kinetic and potential energy, as well as energy exchange between different muscle groups. These synergies can easily be compromised by the changes in timing characteristics following a brain or spinal cord injury. Abnormal synergy patterns arise due to lack of control over individual muscle groups. Unintentional co-contraction of antagonistic muscles may also lead to abnormal torque generation at the joints. As a consequence of these changes in the neuromuscular system, various gait abnormalities take place. Reduced comfortable walking speed (CWS) and/or cadence are common in ambulatory patients. In addition, for fear of falling, longer stance phase of the unimpaired leg can also be observed. This results in asymmetrical gait patterns that are inefficient.

The deviations from a healthy gait pattern can be classified into two major groups: primary gait deviations and secondary gait deviations. Primary gait deviations are a direct consequence of the underlying impairment and include stiff-legged gait and drop foot. Stiff legged gait is defined as reduced knee flexion during swing, and is a common primary gait deviation observed in ambulatory patients. The limited toe-clearance poses the risk of tripping over. Stiff-legged gait leads to a gait that is inefficient, unaesthetic, and discomforting. Drop foot is the inability to lift the foot. The ankle flexor muscles are responsible for this motion (or lack thereof). It may cause failure to clear the ground during swing, or result in slapping the ground during heel-strike.

Secondary gait deviations develop as individuals compensate for their primary gait deviations. These compensatory strategies inevitably cause substantial alterations in their gait patterns. For example, limited flexion of the knee and/or the ankle results in insufficient toe-clearance during swing. Secondary gait deviations include hip hiking and hip circumduction. Hip hiking is the excessive elevation of the pelvis during swing. Hip circumduction is the swinging of the leg in an arc (as opposed to a motion confined to the sagittal plane).

Gait Rehabilitation

During the past decade, the field of rehabilitation has witnessed an increasing interest for the clinical use of robotic systems; particularly in the treatment of neurological ailments such as stroke and traumatic brain injury. Stroke survivors typically receive intensive, hands-on physical and occupational therapy to encourage motor recovery. Manual treadmill locomotor training with partial body weight support (BWS) approach has been proven effective in improving gait of poststroke patients. However, manual treadmill training relies on the skill and availability of a physical therapist. Even with the BWS systems, gait training is physically labor intensive. The intensive training required for motor learning is at odds with the availability and cost of a specialized therapist. The scarcity of resources is exacerbated in cases that require a second, or even a third therapist. For instance, for the retraining of a patient who displays hip hiking due to limited knee flexion, one therapist is needed to guide the knee and another one to control the pelvic obliquity. In such cases, it is an additional challenge for the therapists to maintain coordination.

Considering the physical effort involved in such exercises where therapists continually guide the legs and the torso of the patient, robotic neurorehabilitation devices present a great potential as an assistive tool for clinicians by reducing their physical burden. Indeed, some of these systems have already been adopted in clinical practice. Other advantages of robotic systems when compared to manual physical therapy include higher precision and repeatability, and quantitative monitoring of patient's progress via sensors. These factors result in faster and greater level of functional recovery, thus leading to an improvement in patient's level of independence and quality of life.

Maintaining stability during gait is a major concern for most ambulatory patients. In such cases, they are often prescribed stance-control orthotic braces to improve stability. However, conventional orthotic braces such as ankle foot orthoses (AFOs) or knee orthoses (KAFOs) typically address the problem of stability by limiting the patient's range of motion (RoM). Such limitation consequentially instigates abnormal gait patterns. For instance, a KAFO designed to increase stability by limiting knee flexion would result in stiff-legged gait. Because of this primary gait deviation, foot clearance would be compromised during the swing phase. Consequently, the patient would develop compensatory strategies such as hip-hiking and/or circumduction (i.e. secondary gait deviations) to provide ground clearance for the foot. Due to their negative impact on gait patterns, the use of conventional orthotic braces is limited to cases where maintaining stability holds a higher priority than restoring healthy gait patterns. On the other hand, robotic knee orthoses have the potential to overcome the aforementioned limitations by facilitating the knee movement instead of restricting it.

Robotic gait retraining exoskeletons differ from the conventional orthoses at a very fundamental level: robotic gait re-trainers work towards reinforcing a desired gait pattern and reducing the patient's dependence on assistive technologies; whereas traditional orthoses only mask the symptoms. All rehabilitation robots apply forces on the patient's limbs in one way or the other. One such system is a mechanical exoskeleton worn by an operator. Anthropomorphic exoskeletons attempt to mimic the kinematic structure of the human skeleton. As they work in parallel with the user's limbs, mechanical limits can be implemented directly, and the risk of collisions is eliminated. However, the joints should be accurately aligned with that of the user to prevent shear forces. In joints with a single degree of freedom (DoF), such as the knee joint, it is only a matter of adjusting the exoskeleton limb lengths. Unfortunately, proper alignment is not as straightforward in joints that have more than 1-DoF. For example, the human hip comprises a ball and socket joint that is located inside the body. Since it is not physically possible to coincide the exoskeleton's joints with that of the patient's other mechanical solutions are required. For instance, BLEEX utilizes a remote center of rotation (CoR) design. Another design by Herr et al. comprises a cam and roller mechanism that automatically adjusts its length to compensate for the misaligned abduction/adduction joints while still transferring vertical loads.

Several robotic devices for gait retraining of stroke patients have been developed in the last decade. The Lokomat (Hocoma AG, Switzerland) is a exoskeletal bilateral gait rehabilitation robot with a BWS system. The patient's legs are actuated in the sagittal plane via DC motors coupled to ball screws. A spring-based passive foot lifter helps with ankle dorsiflexion during swing. However, the pelvis is only allowed to translate in the frontal plane. Its therapy methods rely on repetition and task-oriented training.

In contrast to Lokomat, LOPES (LOwer Extremity Powered ExoSkeleton) (University of Twente in the Netherlands) is an example of a new breed of rehabilitation robot that is designed to display low mechanical impedance. Low mechanical impedance is achieved via Bowden cable driven joints that utilize series elastic elements. Series elastic elements add mechanical compliance to the system, which renders higher force-feedback gains possible. In addition to the hip and knee joints that Lokomat controls in the sagittal plane, LOPES features additional actuation of the pelvis in the horizontal plane, as well as hip abduction/adduction. These additional DoF are important, since it is known that fixating the pelvis affects natural walking. All motions of the ankle, and vertical translation of the pelvis are allowed, but are not actuated.

The aforementioned devices control multiple degrees of freedom (DoF) of the patient and can only be used in a hospital setting due to their complex design. There exists lower-extremity exoskeletons that are portable, however most are designed to serve as assistive devices for activities of daily living (ADL) and not for gait retraining eLEGS from Berkeley Bionics is such a device that enables paraplegics to stand up and walk with the use of a gesture based human-machine interface, albeit with help of crutches. Another example is the Tibion Bionic Leg. The Tibion Bionic Leg is a fully portable exoskeletal gait retraining powered orthosis with onboard electronics and battery. The Tibion Bionic Leg can aid the patient in sit-to-stand, overground walking, and stair-climbing exercises during which the amount of assistance can be programmed by the therapist via the interface panel on the front. The frame is constructed of composite carbon-fiber material. A pressure sensor at the bottom of the foot provides the control algorithm with the weight-on-foot information. Additional sensors for knee angle measurement, actuator force, motor currents, battery voltage, and internal temperatures are present. The mass of the Tibion Bionic Leg is concentrated around the knee joint, which introduces unusual inertial torques on the hip joint during swing. In addition, there is also no AFO or pelvic brace that help transfer the forces to the ground, and therefore the entire weight of the device is carried by the impaired leg.

The current treadmill-based gait retraining systems like Lokomat, do not facilitate overground locomotion. While existing robotic devices provide a valuable asset for rehabilitation hospitals, their high cost limits the number of training sessions the patients receive during rehabilitation. On the other end of the spectrum, there are examples of portable lower extremity exoskeletons. However, these devices are designed to serve as assistive devices for activities of daily living, and not for gait retraining. Thus there exists a technological gap for a new breed of rehabilitative orthotic devices that maintain the positive attributes of the treadmill devices while downplaying their high cost. In addition, there exists a need for portable gait retraining systems that facilitate overground locomotion rather than just serving as assistive devices for activities of daily living.

BRIEF SUMMARY

Methods and systems for providing portable gait retraining systems that facilitate overground locomotion is provided. A wearable and portable assistive tool for gait neuro-rehabilitation which targets primary gait deviations (e.g. knee hyperextension during stance and stiff-legged gait during swing phase) by reinforcing a desired gait pattern via corrective torque-fields applied around the knee joint is described. A sensorized yet unactuated brace worn on the unimpaired leg is used to synchronize the target trajectory based on the user's intent, thus facilitating a patient-driven exercise regimen (as opposed to a fixed playback independent from the patient's effort).

In one embodiment a lower extremity exoskeleton for gait rehabilitation is described and, among other components, comprises a pelvic brace, an unactuated leg brace, an actuated leg brace. The unactuated leg brace is rotatably connected to the pelvic brace, and further comprises first upper and first lower leg shanks joined by a first rotatable knee joint to provide flexion and extension of the unactuated leg brace, and a sensor for measuring knee flexion and extension angles of the first rotatable knee joint. The actuated leg brace is rotatably connected to the pelvic brace, and further comprises second upper and second lower leg shanks joined by a second rotatable knee joint to provide flexion and extension of the actuated leg brace, and a means for creating a torque around the axis of rotation of the second rotatable knee joint. An impedance controller computes a desired knee angle at the first rotatable knee joint based in part on the sensor measurements and commands a torque at the second rotatable knee joint based in part on the desired knee angle.

In another embodiment a computer generates a desired joint angle estimate by measuring at least one gait related physiological parameter of a patient, estimating the gait phase based on at least the one gait related physiological parameter, estimating the cadence based on at least the one gait related physiological parameter, selecting a new reference gait trajectory based on at least the estimated cadence; and computing a desired joint angle based on the estimated gait phase and the new reference trajectory.

These and other features will become readily apparent from the following detailed description where embodiments of the invention are shown and described by way of illustration.

BRIEF DESCRIPTION OF THE SEVERAL VIEWS OF THE DRAWINGS

For a more complete understanding of various embodiments of the present invention, reference is now made to the following descriptions taken in connection with the accompanying drawings in which.

DETAILED DESCRIPTION

The Active Knee Rehabilitation Orthotic System (ANdROS) is a wearable and portable assistive tool for gait rehabilitation and monitoring of people with motor control deficits due to a neurological ailment, such as stroke. ANdROS reinforces a desired gait pattern by continually applying a corrective torque around the knee joint, commanded by a impedance controller. A sensorized yet unactuated brace worn on the unimpaired leg is used to synchronize the playback of the desired trajectory based on the user's intent. The device is mechanically grounded through two ankle foot orthoses (AFOs) rigidly attached to the main structure, which helps reduce the weight perceived by the user.

Lower Extremity Exoskeleton

Figure 1:
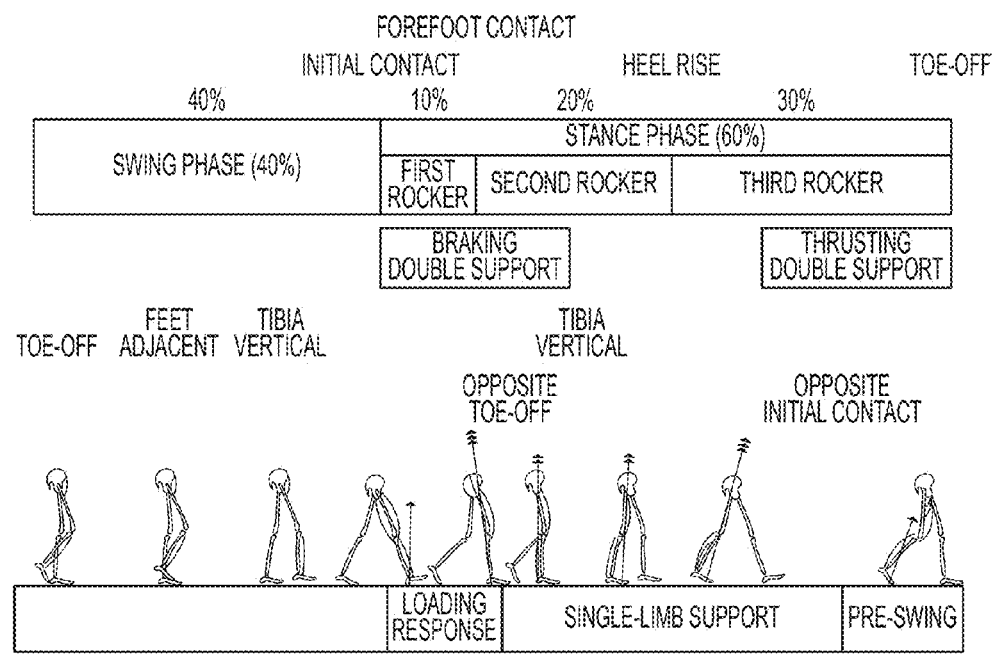
FIG. 1 shows the phases and subphases of gait.
Figure 2:
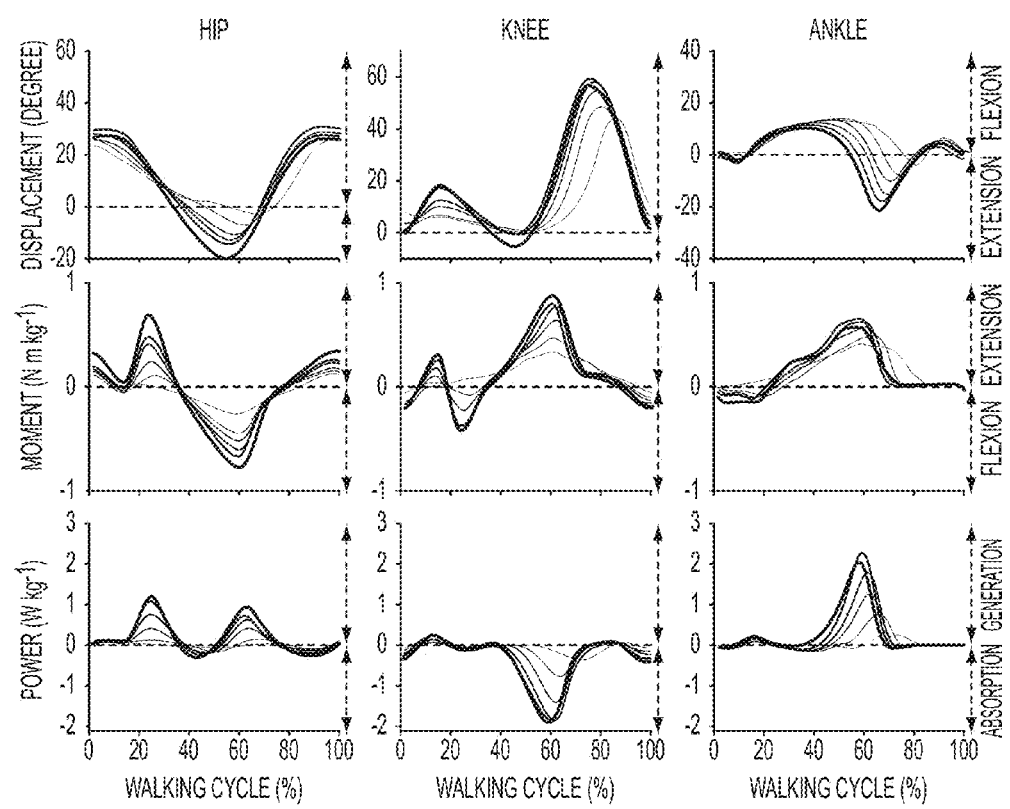
FIG. 2 shows the mean trajectories of the angle, velocity, and power of the hip, knee, and ankle joints as a function of gait cycle.
Figure 3:
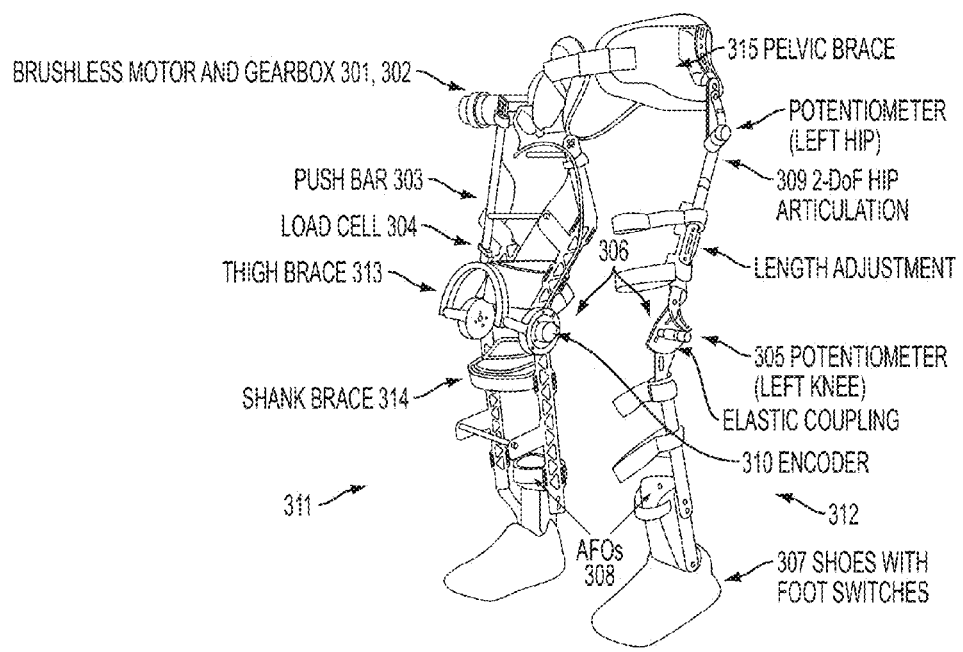
FIG. 3 is a front view perspective drawing of a lower extremity exoskeleton.

In accordance with an embodiment of the present invention, FIG. 3 is a front view perspective drawing illustrating a lower extremity exoskeleton 300. The exoskeleton frame consists of two separate leg braces: an actuated brace 311 attached to the impaired leg, for example, via rigid straps, and a sensorized unactuated brace 312 attached to the healthy leg, for example, via elastic straps. Each brace includes a thigh portion 313, a shank portion 314, and an ankle foot orthosis (AFO) 308. Each brace 311 and 312 is attached to the pelvic brace 315 through a 2-DoF hip articulation 309 which allows for abduction/adduction and flexion/extension of the hip joint.

The actuated brace 311 is driven by a brushless DC motor 301 coupled to a gearbox 302 that is located next to the pelvis, to reduce the moving mass and keep the center of mass (CM) of the exoskeleton close to the wearer's CM. The exoskeleton can be powered by a battery that is worn by the user (not shown). The brushless DC motor is controlled using a brushless motor amplifier (not shown) and the desired torque output of the motor is commanded by an external analog voltage command. The torque generated by the motor is transferred to the knee joint by means of a push bar 303 that features a quick disengagement mechanism. A tension/compression load cell 304 at the end of the push bar measures the interaction forces between ANdROS and the user. High precision potentiometers 305 are used to measure the knee and hip flexion/extension angles of the unimpaired leg. An incremental encoders (not shown) and rotary potentiometer 305 are placed on either side of the knee joint 306. In addition, the shaft angle of the motor is measured with a digital encoder 310. Foot switches 307 can be embedded inside the sole of the shoes to be used as a distinct reference point in gait analysis, and to confirm the accuracy of human-machine synchronization. The data acquired from these sensors are used in synchronization of the robot with the user. An impedance controller (not shown) uses the sensor data in a feedback loop that computes a desired knee angle and a desired torque.

In one or more embodiments, the brushless DC motor 301 is an MCG 1B23000-E1, the brushless motor amplifier (not shown) is a Xenus XSL servo amplifier from Copley Controls, Inc, and the gearbox 302 is an Anaheim Automation GBPH-0602-NO-040. Brushless DC motors display high power efficiency and torque density at the cost of complicated controls. Brushless motors rely on semiconductor switches, instead of brushes, to turn stator windings on and off at the appropriate time. The process is called electronic commutation. The correct timing of commutation is assisted by knowledge of the shaft angle. Traditional "six-step" (or trapezoidal) commutation relies on hall effect sensors for its phase information and many brushless DC motors come integrated with three hall-effect sensors. However, the resolution of the shaft angle that can be achieved from such a configuration is 60°. Non-ideal phase commutation results in the cogging effect (e.g. fluctuations in motor torque output). Sinusoidal commutation relies on higher resolution phase information, and consequently generates smoother torque output. A 2048 pulses per revolution (ppr) digital encoder 310 is used for precise measurements of the shaft angle. The brushless motor amplifier is used for the sinusoidal commutation and torque control of the brushless motor 301.

Figures 19A, 19B:
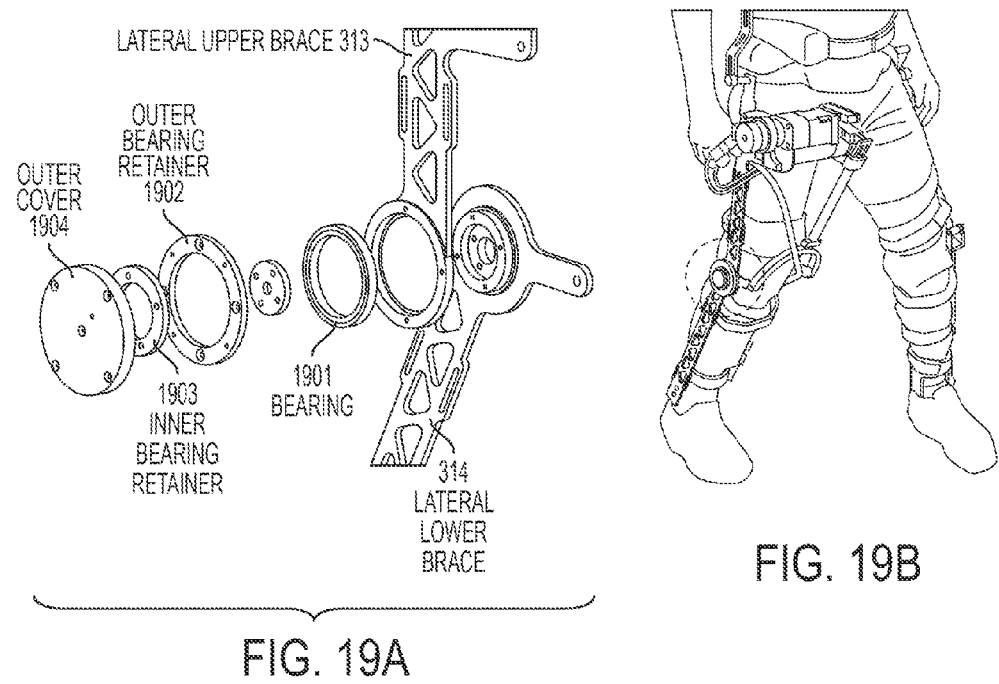
FIG. 19 is an exploded diagram of a knee joint.

The torque generated by the motor is transferred to the knee joint by means of a push bar 303. FIG. 19 shows the knee joint assembly which includes a bearing 1901, an outer bearing retaining ring 1902, an inner bearing retaining ring 1903, and an outer cover 1904. The stainless steel ball bearing 1901 located at the knee joint provides a smooth interface between the thigh 313 and shank 314 components. In addition, the symmetrical structure of the actuated brace applies torque to the knee from both medial and lateral sides of the leg, thus eliminating the twisting effect, which would occur in a single-sided design.

Figure 4:
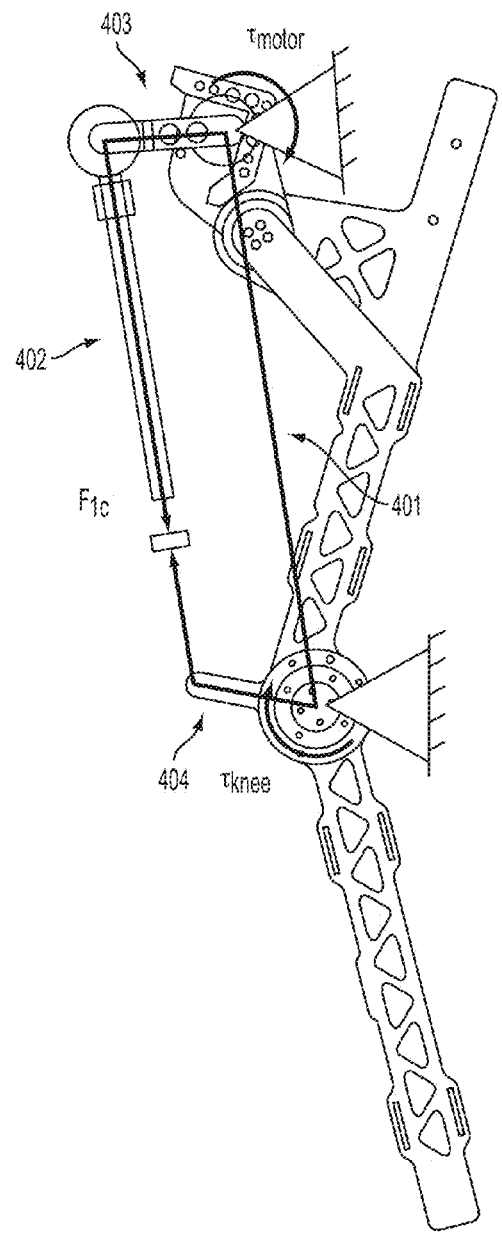
FIG. 4 is an elevation view of a four bar linkage.

The push bar 303 mechanism of ANdROS is basically a four bar linkage, which is shown in more detail in FIG. 4. The four bar linkage is composed of four bars or links connected in a loop with four joints. The joints are configured so the links move in parallel planes. The frame link 401 is the fixed link in the push bar 303 mechanism and is located between the brushless DC motor 301 and the knee joint 306. The link opposite the frame is called the coupler link 402, and the links which are hinged to the frame link are called side links. One side link is the input link 403 and the second side link is the output link 403. When a force is applied to the input link 403, the force is transmitted through the coupler link 402 and is applied to the output link 404.

Figure 20:
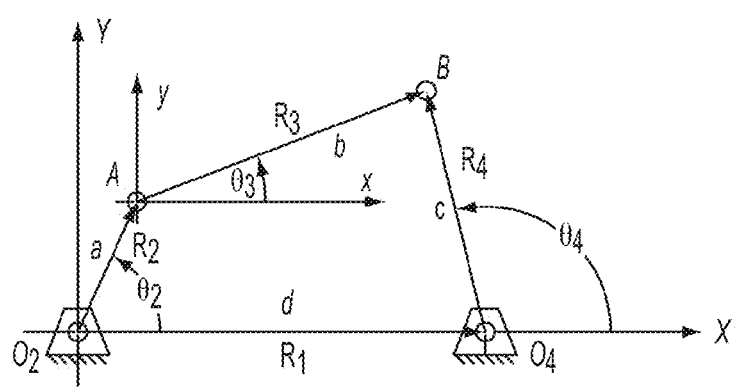
FIG. 20 is a force diagram of the four bar linkage of FIG. 4.

FIG. 20 is a force diagram of the push bar mechanism. The relationship between the input angle (i.e. gearbox shaft) and output angle (i.e. the knee joint) can be found by:

$$\theta_4 = 2\tan^{-1}\left(\frac{-B \mp \sqrt{B^2 - 4AC}}{2A}\right)$$

where:

$A = \cos\theta_2 - K_1 - K_2\cos\theta_2 + K_3$ $B = -2\sin\theta_2$ $C = K_1 - (K_2 + 1)\cos\theta_2 + K_3$ and -continued $$K_1 = \frac{d}{a}$$

$$K_2 = \frac{d}{c}$$

$$K_3 = \frac{a^2 - b^2 + c^2 + d^2}{2\,ac}$$

Figure 16:
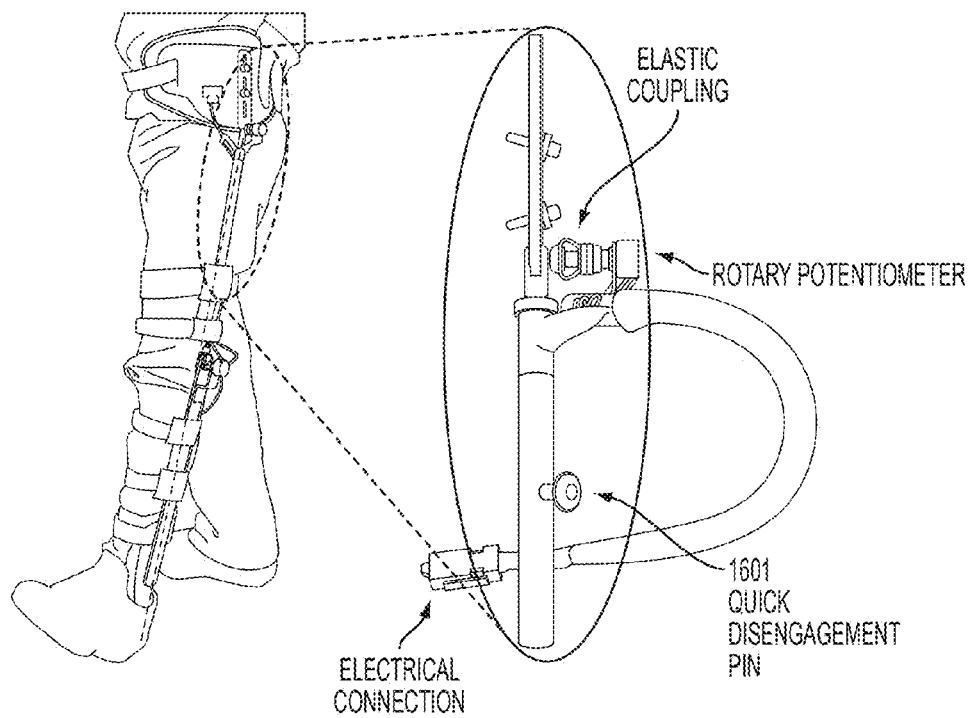
FIG. 16 is a side view of a quick disengagement mechanism used to separate the upper and lower portions of a lower extremity exoskeleton.
Figure 17:
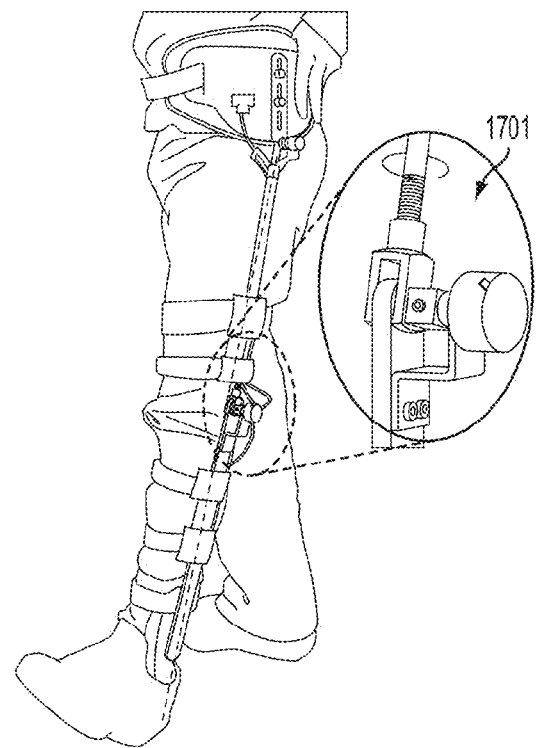
FIG. 17 is a side view of the knee rotation mechanism of a lower extremity exoskeleton.
Figure 18A:
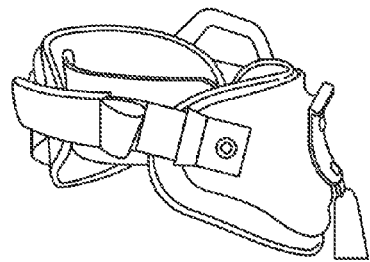
FIG. 18 shows exemplary attachment devices for connecting the exoskeleton to the patient.
Figure 18B:
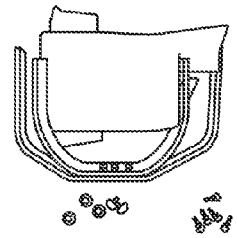
Figure 18C:
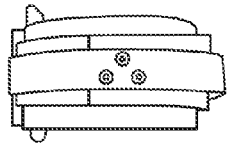
Figure 18D:

The push bar 303 includes a quick disengagement mechanism shown in FIG. 16 and a threaded rod shown in FIG. 17. The quick disengagement mechanism includes a disengagement pin 1601. When this pin is removed the upper and lower portions of the exoskeleton can be separated. By disengaging the lower part of the exoskeleton from the power train, easy adjustment during donning/doffing is possible. The mechanical advantage of the linkage, and the RoM of the output joint (e.g., the knee joint) is dependent on the linkage lengths in the push bar 303. A threaded rod 1701 at the distal end of the push-bar 303 grants slight adjustment of the linkage length, allowing for optimization of the mechanical advantage and RoM. This adjustment can be used to relax the kinematic constraints on the exoskeleton structure once a closed kinematic loop is formed using the 2-legged exoskeleton, the attachment to the feet and through them to the ground. The adjustment in length provides one more degree of "passive" freedom so that the human motion is not constrained from the closed kinematic chain of the exoskeleton that has fewer degrees of freedom.

Referring back to FIG. 3, a tension/compression load cell 304 at the end of the push bar measures the interaction forces between ANdROS and the user. In some embodiments the load cell 304 is an Interface SML-100-10. The load cell is located proximal to the knee joint to maximize the amount of mass between the motor and itself, whose apparent inertia is reduced by force feedback. The brace 312 worn on the unimpaired leg measures the knee and hip flexion/extension angles via high precision potentiometers 305. An incremental encoder (not shown) and a rotary potentiometer 305 are placed on either side of the knee joint 306. The rotary encoder provides high accuracy (0.088°) and noise free measurement of the knee angle, which are properties used in calculating digital derivative for velocity estimation. The potentiometer 305 is used to initialize the incremental encoder's position, and also provide fail-safe operation. The data acquired from these sensors are used in synchronization of the robot with the user. Foot switches 307 are embedded inside the sole of the shoes to be used as a distinct reference point in gait analysis, and to confirm the accuracy of human-machine synchronization.

The exoskeleton should be attached to the body so that there is minimal play (migration) with respect to the human tissue, yet still be comfortable to wear. The actuated brace of ANdROS is attached to the user's body at four locations (i.e. hip, thigh 313, shank 314, and ankle 308) to prevent the migration effect. FIG. 18 shows exemplary attachment devices. The weight of the exoskeleton and the user is transferred to the ground through the AFOs 308. The symmetrical structure of the actuated brace applies torque to the knee from both medial and lateral sides of the leg, thus eliminating the twisting effect that would occur in a single-sided design. A stainless steel ball bearing located at the knee joint (discussed above with reference to FIG. 19) provides a smooth interface between the thigh and shank components.

In any joint, the center of rotation (CoR) of the exoskeleton can be selected to coincide with the wearer's joints to prevent unintended moments and forces on the limbs. Therefore, the thigh and shank components are slotted for adjusting the distance from hip to the knee joint and from the knee joint to the ankle joint, respectively. The brace is secured to the leg via double elastic straps at the thigh 313, shank 314, and AFO 308.

Figure 5:
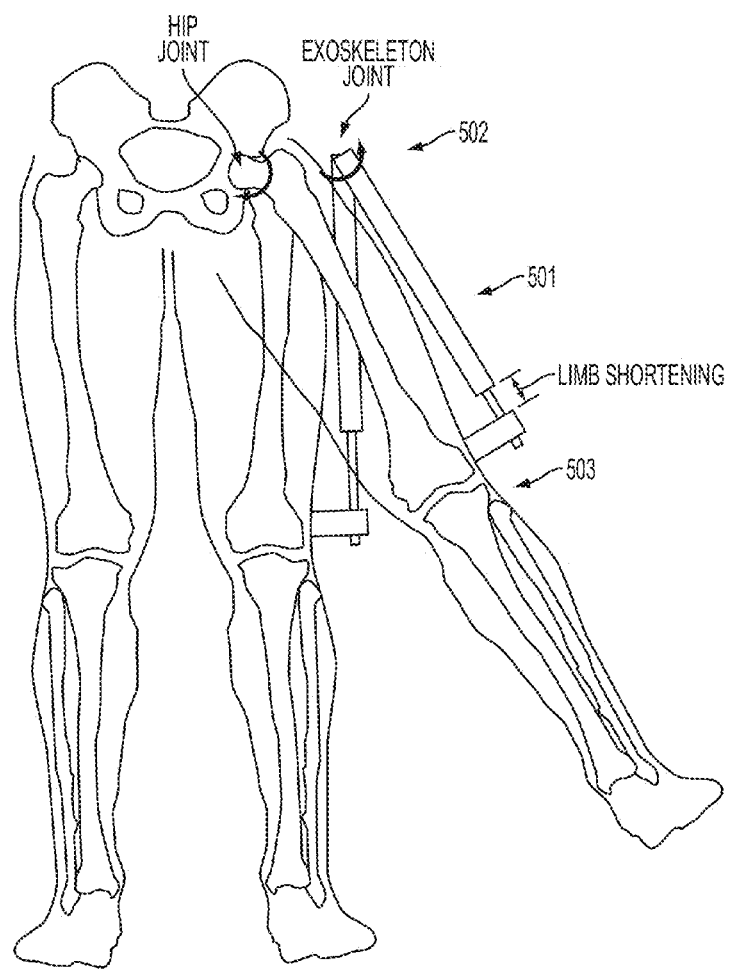
FIG. 5 is a front view drawing showing the center of rotation for a hip and an exoskeleton.

In the presence of a discrepancy between the anatomical CoR of the user and the exoskeleton's CoR, the exoskeleton structure will be forced to shorten during abduction. Since it is not physically possible to coincide the hip joint of the exoskeleton with that of the patient's, this effect can be accounted for to prevent undesired forces on the pelvis. FIG. 5 shows that this effect can be eliminated or minimized by adding a telescopic structure 501 that can freely slide along the length of the leg at the expense of vertical load bearing capability. The telescopic structure 501 is located between the hip joint 502 and the knee joint 503. In this figure, the anatomical CoR and exoskeleton CoR are not coincident. During abduction the telescopic structure will shorten as the users leg rotates around the anatomical CoR and the exoskeleton rotates around its CoR.

Figure 6:
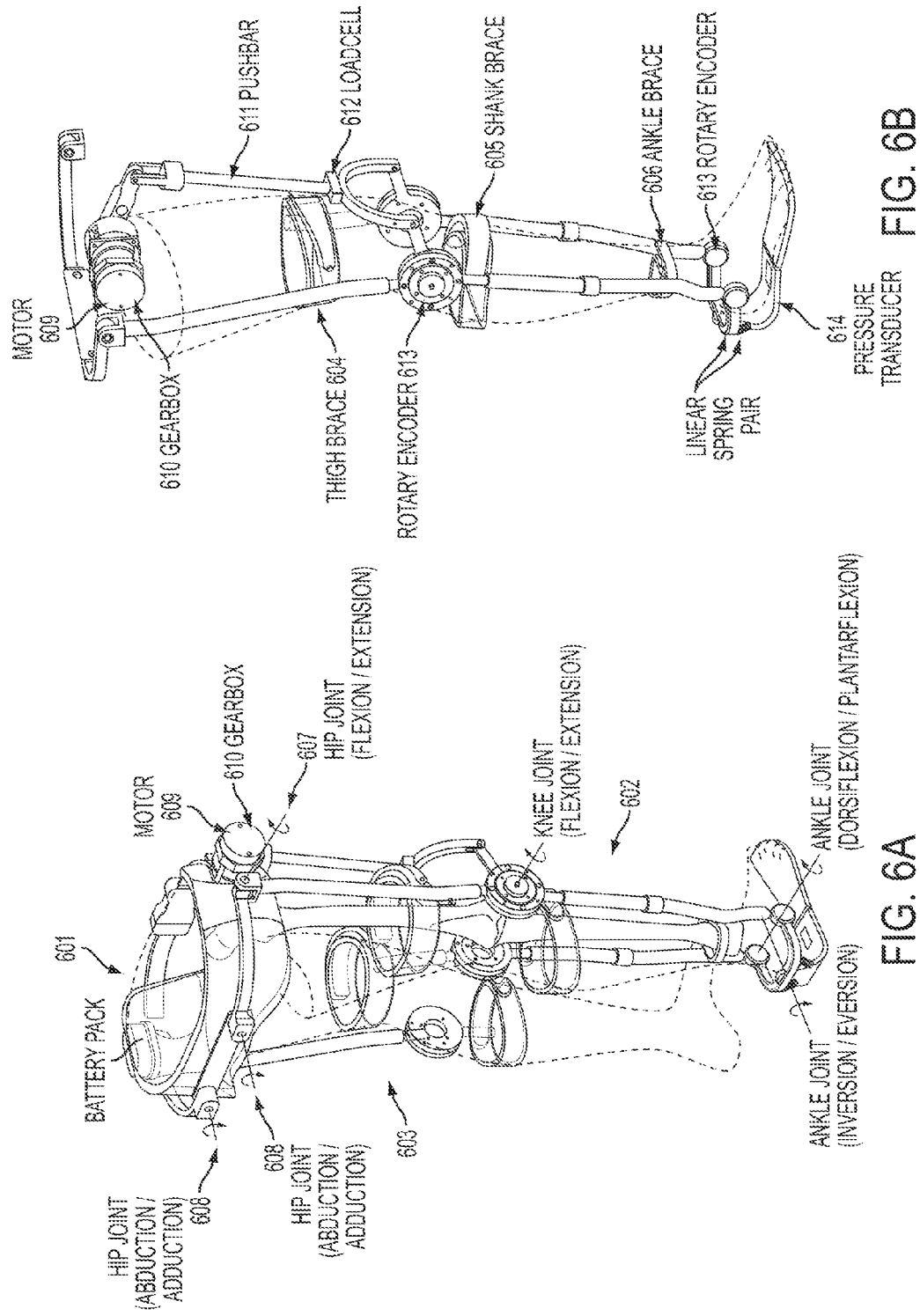
FIG. 6 is a front view perspective drawing of a lower extremity exoskeleton.

FIG. 6 shows an alternative embodiment of a lower extremity exoskeleton. The exoskeleton frame consists of a pelvic brace 601 and two separate leg braces: an actuated brace 602 attached to the impaired leg via rigid straps, and a sensorized unactuated brace 603 attached to the healthy leg via elastic straps. Each brace includes a thigh portion 604, a shank portion 605, and an ankle foot orthosis (AFO) 606. Each brace 602 and 603 is attached to the pelvic brace 601 through a pair of hip joint that allow for flexion/extension 607 and abduction/adduction 608.

Similar to the first embodiment, the actuated brace 602 is driven by a brushless DC motor 609 coupled to a gearbox 610. The torque generated by the motor is transferred to the knee joint by means of a push bar 611. A tension/compression load cell 612 at the end of the push bar measures the interaction forces between ANdROS and the user. High precision potentiometers and encoders (not shown) are used to measure the ankle, knee, and hip flexion/extension angles. In addition, the shaft angle of the motor is measured with a digital encoder 613.

The centers of rotation of the exoskeleton frame are designed to conform to the biological mechanics of the human lower extremity to eliminate undesired torques due to joint misalignment. The hip and ankle joints are simulated by a remote CoR design. For example, the intersection of the hip abduction/adduction and flexion/extension axis can be adjusted to conform to the CoR of the patients hip. To avoid migration, the exoskeleton is firmly attached to the wearer's body via braces located at the hip, thigh 604, shank 605, and ankle 606. The interaction torque around the knee is estimated from the load cell 612 located at the end of the pushbar, and the apparent inertial of the components between the motor and the load-cell is reduced by force-feedback. Additional sensors located at each joint (including the ankle) measure joint angles, which are used for controls and gait monitoring. A pressure transducer 614 located at the sole of the foot is used for estimating gait phase. An additional accelerometer may be included to measure vertical hip position, which would provide additional reliable information for gait phase estimation.

Impedance Controller

The control strategies of rehabilitation robots differ significantly from that of conventional industrial manipulators. One major distinction is that the environment that the robot interacts is a human, with varying system dynamics. Another difference is due to the recent trend in patient-centered exercise regimens, where the robot adapts its behavior based on the patient's effort.

Mechanical impedance (or simply impedance) is defined as the force response of a system to an imposed motion. Loosely speaking, impedance is the dynamic generalization of stiffness, and is defined as a complex function:

$$Z(\omega) = \frac{F(\omega)}{\dot{x}(\omega)}$$

Instead of defining the target position or force (as in position and force controllers, respectively), impedance control defines the dynamic behavior of the robot; which is independent from the environment it interacts with.

Figure 7:
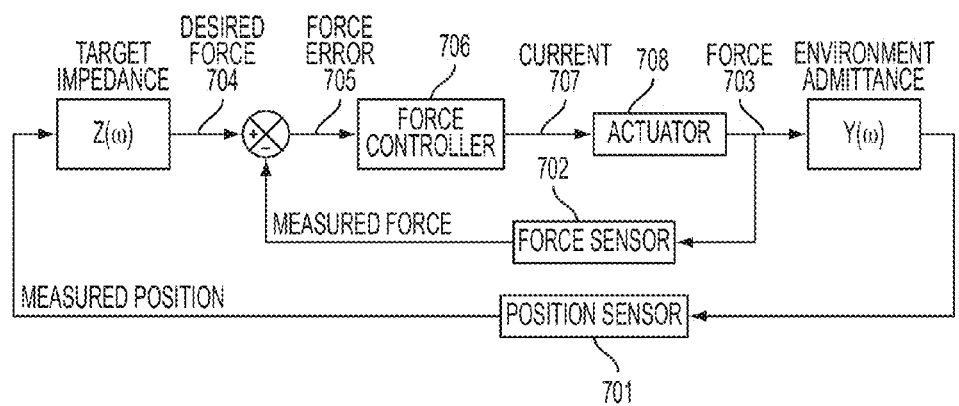
FIG. 7 is a block diagram of a generic impedance controller.

FIG. 7 shows the block diagram of a generic impedance controller. The outer "position-loop" defines the desired force based on the target impedance and the position feedback. In particular, a position sensor 701 is used in a feedback loop to provide measured position information (e.g. the output) as an input to the controller.

The main function of the inner force-loop is to compensate for the actuator's own dynamics, thus moving it closer to an ideal force source. The inner "force-loop" brings the actuator closer to a pure force source, by using force feedback to reduce the apparent inertia of any mass between the actuator and the sensor. In particular, the force sensor 702 measures the force supplied by actuator 703. This measurement is used in the inner "force-loop" and is subtracted from the desired force 704 computed in the outer loop. The resulting error force 705 is passed to the force controller 706 which, in turn, supplies the desired current 707 to the actuator 708. The actuator then, if necessary, changes the applied force and position which is then measured and passed back through the inner and outer feedback loops.

When applied to gait rehabilitation, an impedance controller creates a virtual dynamic system between the patient's leg and a target gait trajectory. For instance, a zeroth-order impedance model would act as if the patient's leg is attached to a spring moving along a path; whereas a first-order impedance model would simulate a spring and a damper. If the patient followed the ideal reference trajectory with accuracy, the target interaction force would be zero. In practice, however, the quality of the force source is limited by the actuator's force fidelity.

Figure 8:
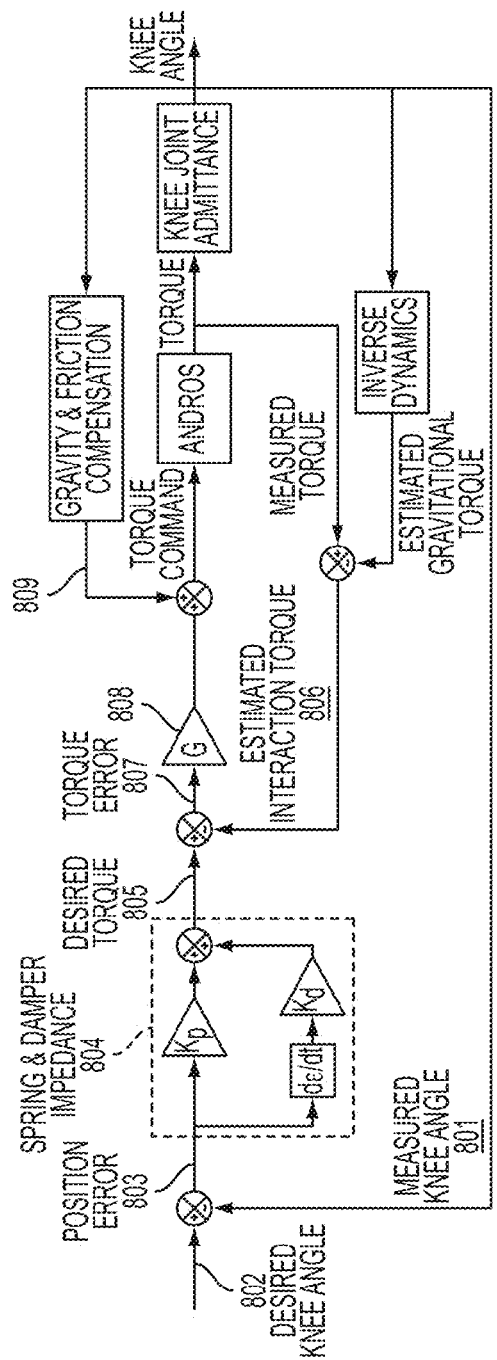
FIG. 8 is a block diagram of an additional impedance controller.

The block diagram of the impedance controller implemented on ANdROS is illustrated in FIG. 8. The outer position loop mandates the desired interaction torque, based on the deviation from the desired trajectory and the impedance parameters. Specifically the measured 801 and desired knee angles 802 are compared and produce a position error 803. The position error is supplied to the spring/damper model 804 of the patient's leg which generated a desired torque 805.

The inner force loop is a simple proportional feedback controller with feedforward terms to compensate for gravity and motor friction. The measured torque 806 and the desired torque 805 are compared and produce a torque error 807. A gain 808 is applied and the output is then compared with gravity and friction feedback measurements 809. The resulting requested torque is passed to the ANdROS (e.g. the brushless motor and amplifier). In addition, the force feedback signal is conditioned because seemingly harmless oscillations will be amplified by the closed-loop controller, which in turn can push the system towards instability. The unamplified load cell signal is carried to an amplifier with built-in analog filter (not shown) via double-shielded cables.

Figure 9:
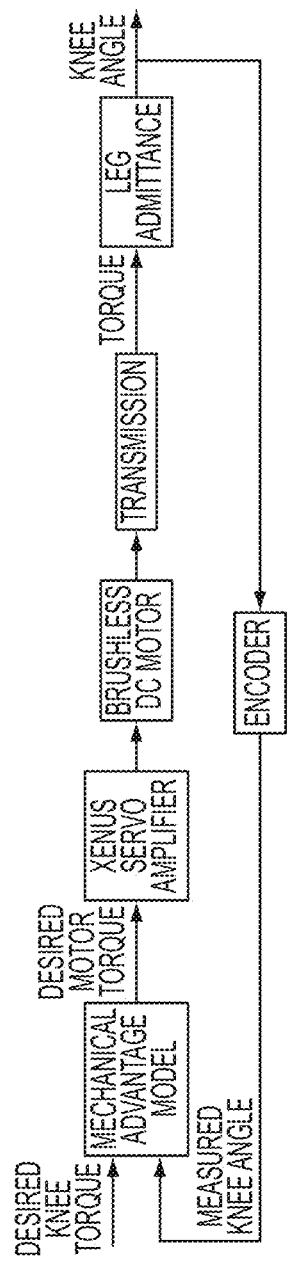
FIG. 9 is a block diagram of the torque transfer provided by the four bar linkage.

Most of the friction in the system arises from the gearbox, and is easily compensated for by a feedforward torque that is proportional to the motor velocity. Implementing gravity compensation, however, is not that straightforward. Calculating the torque resulting from the mass of the four-bar linkage as a function of the knee angle is very complicated. Instead, the holding torque at discrete angles has been experimentally identified. The counter-torque to compensate for gravity is then calculated using the equation of the fitted curve using the experimental data. It should also be noted that the transformations accounting for the mechanical advantage of the four-bar linkage are excluded from the control diagram shown in FIG. 8. A more detailed representation of the actual torque transfer is depicted in FIG. 9.

As described above, multiple digital encoders are installed on ANdROS; one on the knee joint and one on the motor shaft. As shown above in FIGS. 7 and 8, a first-order impedance model requires the knowledge of position, and its time derivative (i.e. velocity). A common method of estimating velocity from an angle sensor is to differentiate the distance traveled over a known sampling interval. However, when estimating velocity from pulse-encoded position signals, quantization noise can be observed. The effect of quantization noise is pronounced especially at lower velocities, and at small sampling intervals (i.e. high frequencies). It is possible to attenuate the quantization noise by implementing a filter (e.g. moving average), at the cost of time-delay.

A straightforward solution to reduce the quantization noise would be to increase the encoder resolution, but there is a practical limit on the pulses per revolution an encoder can have. Instead, in ANdROS an estimate the velocity at the motor shaft is computed and then this is converted mathematically to an estimate of the knee velocity by using equations that model the four-bar linkage. Since the motor shaft rotates 40 times faster than the gearbox shaft, this approach significantly reduced the quantization noise.

Gait Pattern Adaptation

One additional input to the impedance control loop is the desired knee angle. The desired knee angle is generated from the estimation of gait phase based on a human-machine synchronization algorithm. The synchronization algorithm is a variation of the method proposed by Aoyagi et al. in "A robot and control algorithm that can synchronously assist in naturalistic motion during body-weight-supported gait training following neurologic injury," *IEEE Transactions on Neural Systems and Rehabilitation Engineering*, vol. 15, pp. 387-400, 2007, the disclosure of which is incorporated herein by reference.

The field of clinical gait analysis, defined as the systematic study of human locomotion, has benefited vastly from the recent developments in computerized data analysis systems. Modern gait analysis systems typically consist of several cameras that record the motion path of retro-reflective markers as the patient walks on a platform equipped with force plates that measure ground reaction forces. The acquired data are then post-processed to obtain clinically significant gait parameters. These parameters can be classified into two major groups: kinematic parameters and kinetic parameters.

Kinematics studies the motion of rigid bodies without considering the forces causing motion. In case of gait analysis, kinematic parameters include measurements of joint angles and their derivatives. Gait events such as heel strike and toe off may also be recorded to help normalize the time scale to one full gait cycle. This normalization allows easy comparison of various gait patterns.

Kinetics involves the study of forces that produce movement. Direct measurement of all the forces involved in gait may not always be practical or even possible. Instead, the kinetic parameters of individual joints such as torque, power, and work can be estimated by substituting the joint angles and ground reaction forces into an inverse-dynamic biomechanical model. In addition, electrical activity of the muscles may also be recorded by use of electromyography (EMG) sensors.

Human walking, or bipedal gait in general, is a complicated dynamic process involving the coordination of several mechanisms. Due to this complex nature of walking, gait patterns display variations from one gait cycle to the next. When discussing the control schemes of rehabilitation robots, it has been emphasized that the impedance controller allows deviations from "the" reference trajectory, taking the existence of such an ideal trajectory for granted. However, the assumption of "one trajectory fits all" is an oversimplification. Even though there exists a plethora of studies on the influence of parameters such as walking velocity on gait, the implementation of this collective database to trajectory generation in robotic gait retraining has been rather limited.

Impedance control algorithms that use a single ideal reference trajectory do not explicitly address the variations in the kinematics of gait. Indeed, Aoyagi et al. reported that users suffered from the "beat" phenomenon arising from the interaction of a pair of coupled oscillators (i.e. the human and the robot) with slightly different frequencies. This phenomenon caused the patient to walk out-of-phase with the robot, which resulted in large so-called "corrective" forces associated with the large tracking error. The patients eventually learned to use these unintended forces to their advantage: transforming the intended assist-as-needed therapy (which maximizes voluntary effort of the patient) into active assisted therapy.

As discussed above, active assist therapy reduces the kinematic error associated with a movement, and thus could compromise the learning of altered neuro-mechanical dynamics. To overcome this problem, Aoyagi et al. proposed a synchronization algorithm that adjusts the playback rate of the reference trajectory. The algorithm estimates the gait phase by finding the closest point in an n-dimensional space of kinematic parameters, and low-pass filters the estimate using an integrator feedback loop. The algorithm was implemented on the gait rehabilitation robots PAM and POGO, using the position and velocity signals from all 9 DoFs to constitute the 18-dimensional state space. The authors claim that by using many DoFs, the algorithm is rendered more robust.

Figure 10:
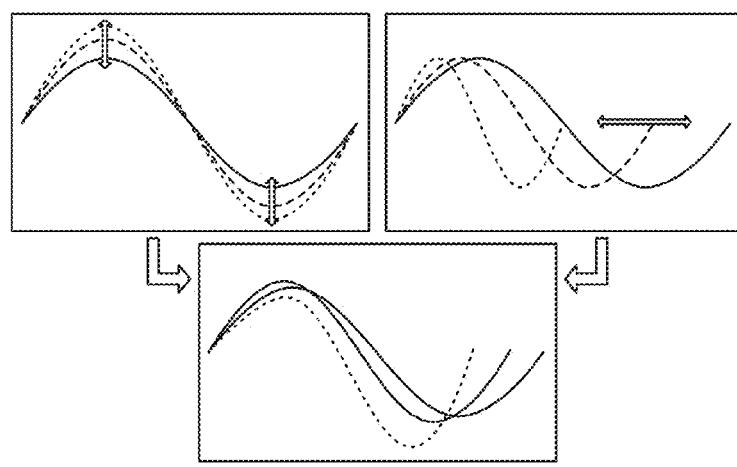
FIG. 10 is a diagram of a gait reference trajectory adjusted in both the temoral and spatial dimension.

By adjusting the playback rate of the ideal reference trajectory, the Aoyagi synchronization algorithm allows adjustment of the reference trajectory only in the temporal space, and does not take changes of the spatial parameters into account. FIG. 10 shows the adjustment of a reference trajectory in the spatial dimension, the temporal dimension, and both the spatial and temporal dimension. The "ideal" trajectory of the knee joint angle is not necessarily identical under different walking conditions (e.g. walking velocity, cadence, and step length). Failing to account for these changes could cause forces that are perturbing rather than corrective. Although the idea of stretching the reference trajectory along the time axis in order to synchronize the robot with the patient was an improvement over the fixed reference trajectory approach, it fails to integrate the complex nature of gait into the robot controller.

In ANdROS, the Aoyagi synchronization algorithm was modified to estimate the instantaneous cadence of the patient in real-time and to provide a modified reference trajectory to the impedance controller that matches the real time cadence of the patient. Cadence is defined as the number of steps per unit time, usually given in steps/min. Step length is defined as the distance between successive heel contacts. In symmetrical gait, left step length is equal to right step length. Walking velocity is the distance travelled per unit time. These three parameters are correlated by the following equation:

walking velocity(m/min)=cadence(1/min)×step length(m)

This shows that at a constant walking velocity, cadence and step length are inversely correlated.

First, data was collected to understand the factors that influence the gait pattern. To this end, joint angle trajectories were recorded while healthy test subjects walked on the treadmill at various cadences (i.e. 70, 80, 90, 100, 110, 120, and 130 steps/min). To make sure that the test subjects were walking at the desired cadence, they were asked to synchronize their rhythm with that of a metronome. A minimum of 30 cycles were recorded using the passive exoskeleton of ANdROS, including flexion/extension angles of the hip, knee, and ankle joints. Joint velocities were calculated using a zero-phase $2^{nd}$-order back-forward digital derivative, which was implemented during post-processing. A computer program was written in MATLAB that automatically extracted individual gait cycles and sorted them based on their cadences.

Figure 11:
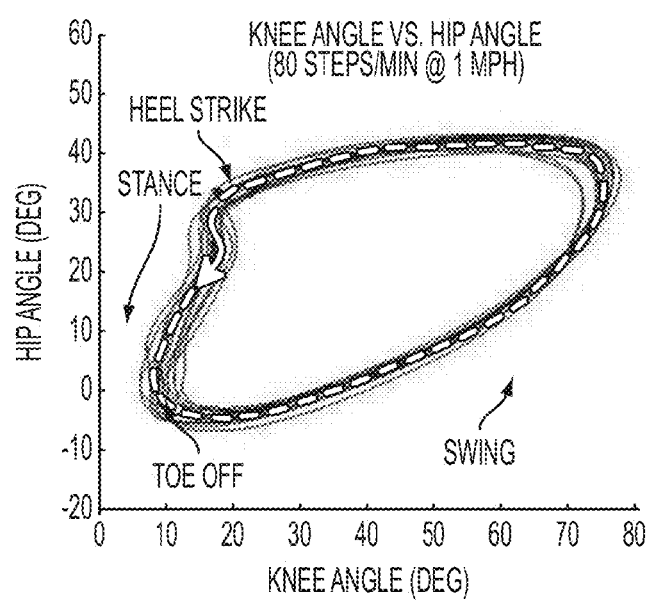
FIG. 11 is a plot of knee angle trajectory versus hip angle trajectory.

FIG. 11 is a plot of the knee angle trajectory versus the hip angle trajectory showing the quasi-cyclic nature of gait. During forward walking, gait parameters follow the path in the counter-clockwise direction. Phases of gait are also shown on the plot. The Aoyagi synchronization algorithm is an N-dimensional generalization of finding the closest point on the plot of the ideal reference trajectory.

Figure 12:
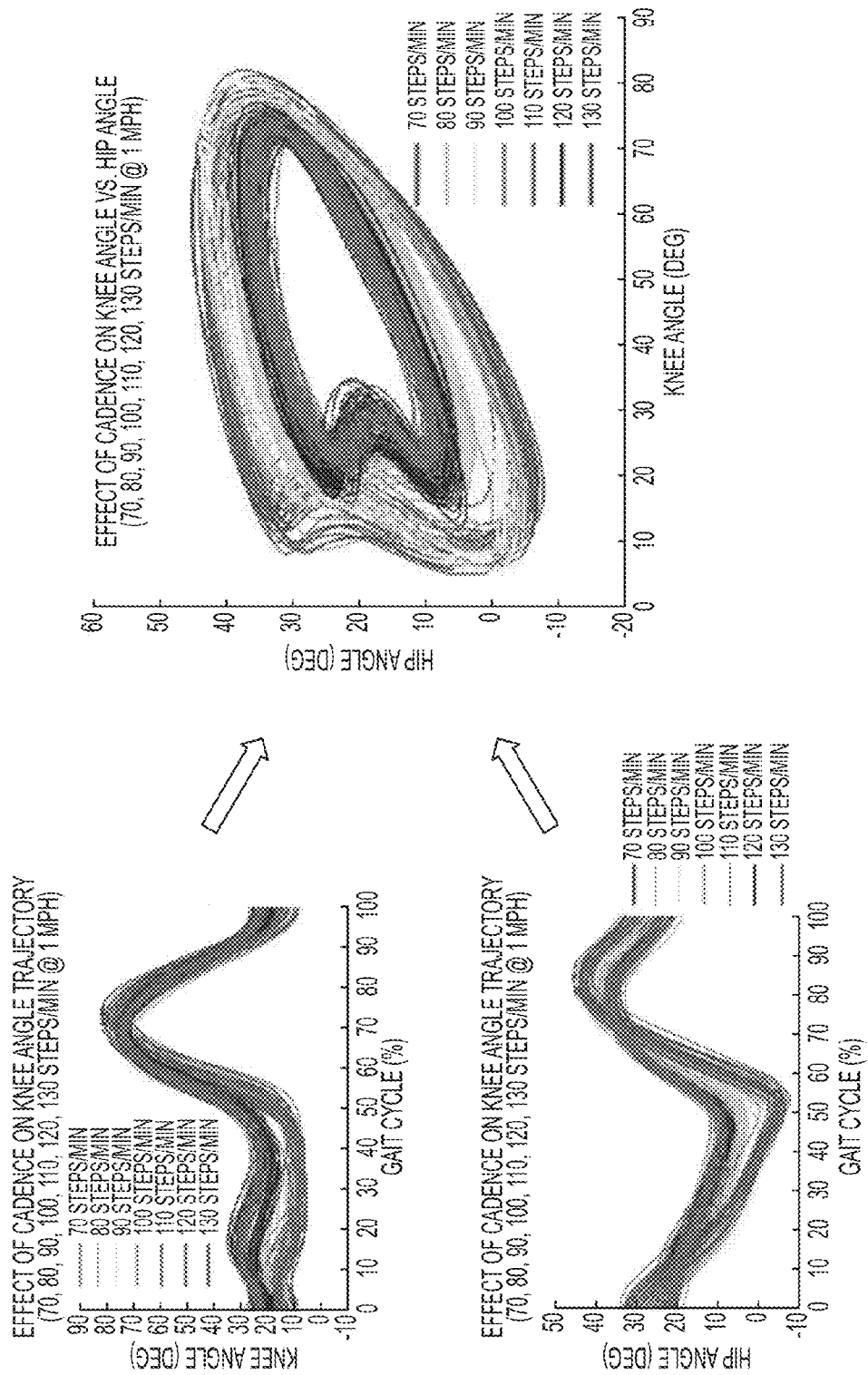
FIG. 12 is a plot showing the effect of cadence on knee angle trajectory and hip angle trajectory

FIG. 12 is a similar plot, showing the effect of cadence on the knee angle trajectory versus the hip angle trajectory. This figure shows that as the cadence of a patient varies, the "ideal" trajectory will change.

Gait Phase Estimation

Figure 13:
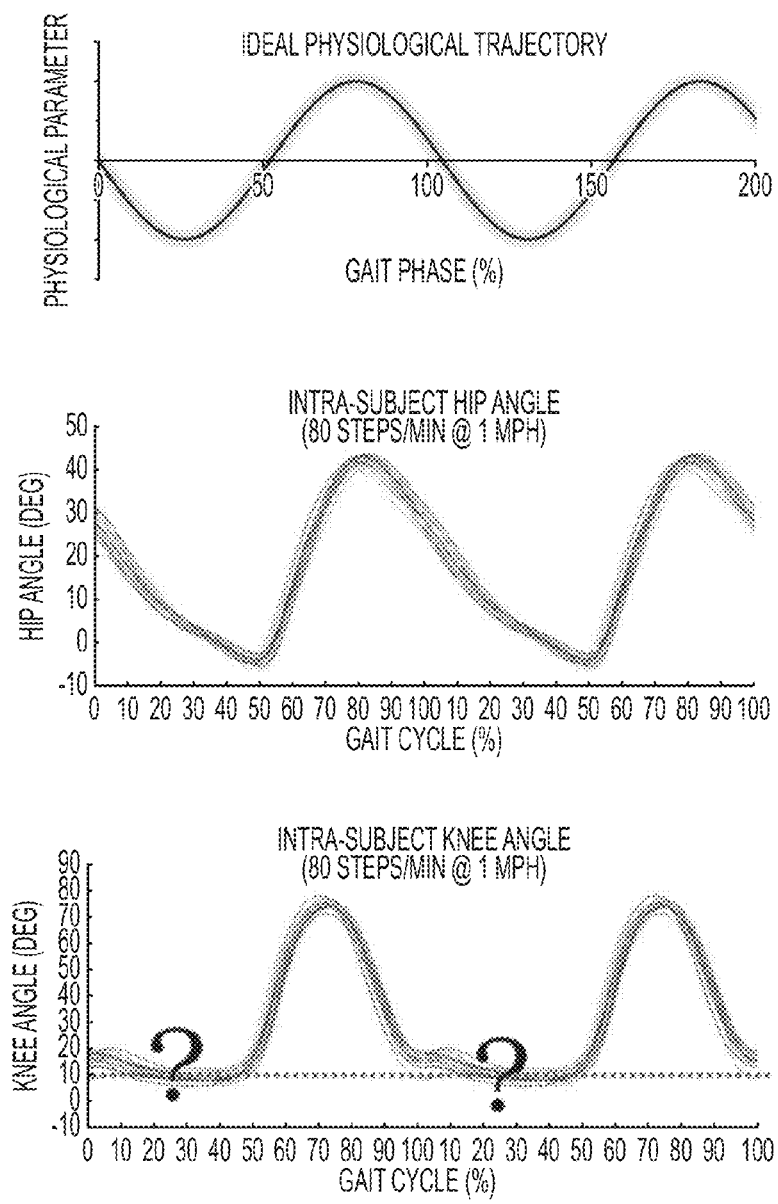
FIG. 13 is a plot of various gait parameters an ideal gait cycle.

The problem of gait phase estimation (GPE) can be defined as the use one or more gait related physiological inputs to approximate the phase of gait at a given instant. At least three physiological parameters can be used for GPE. FIG. 13 shows that a physiological parameter that follows a sinusoid-like trajectory along the gait cycle would be optimal. The hip flexion/extension angle follows a similar trajectory, and thus is a good candidate. On the other hand, the knee flexion/extension angle does not provide any distinct information during stance. But during swing the knee angle follows a second-order parabolic polynomial. Another physiological parameter that is known to display sinusoidal oscillations is the vertical hip position. Because the fitness of a physiological parameter can change within a gait cycle (e.g. knee flexion/extension angle during swing versus during stance), it is reasonable to use phase-dependent weighing functions for each parameter.

The GPE problem can then be defined as an optimization problem with the function to be minimized being:

$$f(\varphi) = \sum_{i=1}^{N} w_i(\bar{\varphi})|x_i^*(\varphi) - x_i|$$

where $\varphi$ is the gait phase, N is the number of measurements employed, w is the weighting function, $\bar{\varphi}$ is the estimated gait phase from the previous calculation, x* is the value of the pre-recorded trajectory corresponding to the gait phase, and x is the measurement of the particular parameter.

ANdROS uses the hip, knee, and ankle positions and their corresponding velocities of the unimpaired leg to estimate the gait phase. None of the measurements of the impaired leg are employed in the GPE algorithm, since actuating the impaired leg based on its own measurements would create redundancy. A preferred embodiment includes weighing the functions proportionally with the absolute value of their derivatives (i.e. rate of change).

The modifications to the Aoyagi algorithm include: a) the use of variable weighing functions that are generated from the absolute value of the derivative of the corresponding trajectory; b) the use of cadence based look-up trajectories in the minimization algorithm; and c) adaptive target trajectories that stretch in the temporal domain based on the estimated gait phase; and vary in the spatial domain based on the estimated cadence.

Figure 14:
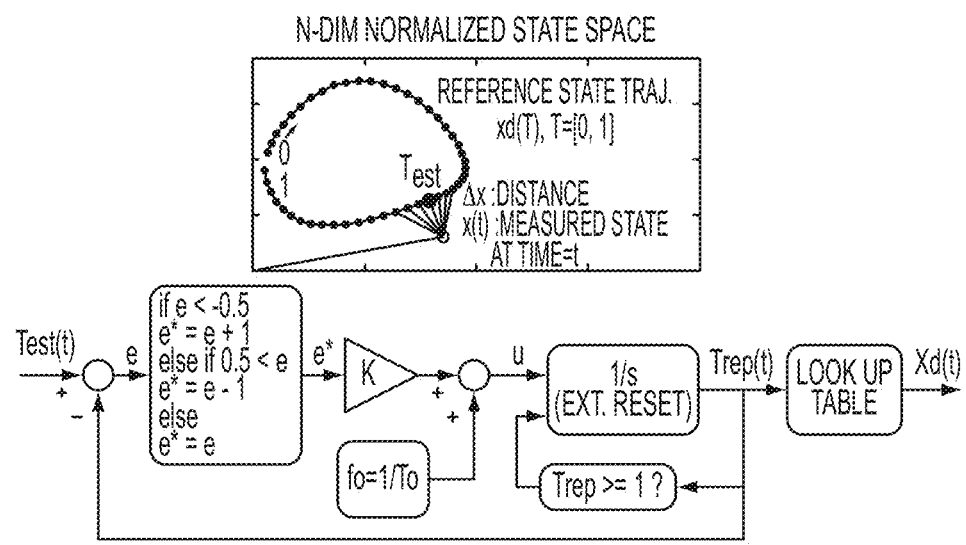
FIG. 14 is a block diagram of the Aoyagi gait estimation algorithm.

FIG. 14 depicts the generic block diagram of the modified Aoyagi algorithm. The gait phase estimation block finds the closest point on the N-dimensional joint state-space based on variable weighing functions. The estimated cadence defines which state trajectory will be taken as a reference for the minimization during this step. After an estimate of the gait phase is obtained, the desired angle is found from the corresponding look-up table. The desired joint angle is then supplied as an input to the impedance controller discussed above.

Future possible modifications to the Aoyagi algorithm include: a) a treadmill with automatic velocity adjustment; b) velocity dependent trajectories in the trajectory generation algorithm; c) an accelerometer to use vertical hip position as a robust gait phase estimation parameter; and d) an optimization algorithm that automatically generates the optimal weighting functions, based on the database of pre-recorded gait trajectories.

Backdriveability

During gait retraining, the corrective forces are applied in response to deviations from the ideal reference trajectory. It follows that when the patient is walking "correctly" the interaction forces between the human and the robot should be ideally zero. In other words, it is desirable that the robot's weight and inertia should be imperceptible by the user. To test how close the system can simulate this behavior, the desired torque was set to zero and the exoskeleton can be oscillated manually. In this mode of operation, called backdrivable mode, the robot applies a torque in the same direction of the motion in an effort to minimize the interaction torque. The actual interaction forces between the user and the exoskeleton can not measured by the load cell that is located on the push-bar, since the forces arising from inertia, weight, and friction of the lower brace are also sensed at this location. Therefore, a secondary load cell (not shown) can be attached to the lower brace during backdrivability testing to estimate the forces that would be perceived by the user at their shank. The secondary load cell is not required during normal usage of ANdROS by the patient.

Additional Embodiments

As discussed above deviations from a healthy gait pattern can be classified into primary gait deviations and secondary gait deviations. It is possible to address primary gait deviations using the lower extremity exoskeleton described above at the same time that secondary gait deviations are being address with pelvic system. For example, the lower extremity exoskeleton could be used to prevent stiff-legged gait (a primary gait deviation), which in turn leads to hip-hiking (a secondary gait. The hip-hiking can be addressed with a pelvic system, such as the systems describe in U.S. Patent Application No. 61/500,797 filed on Jun. 24, 2011 which is incorporated herein by reference. Other pelvic systems that can be used with lower extremity exoskeleton described above include hip rehabilitation robots and body weight support structures, such as those typically used during treadmill training.

In an additional embodiment the lower extremity exoskeleton described above can be combined with a virtual reality system. This can be used to improve the number of modalities involved in the exercise and as a result increase the outcome of rehabilitation. The virtual reality (VR) system will be composed of three hardware components: a head mounted display, a treadmill, and the ANdROS. It will also contain two software components: the VR for Calibration and Evaluation (VRCE) and the VR for Motivation and Enjoyment (VRME). In a preferred embodiment the VR scenes will be built using the Panda3D graphics engine available at http://panda3d.org. All of the software in the VR engine is open source and free to download. The engine can be written as C++ libraries and modules and controlled by scripts written in Python. Panda3D also has comprehensive support for networking that would allow for rich virtual interactions between users.

The VR may be displayed for the patient using a head mounted display (HMD). The HMD will allow the patient to be immersed in the VR environment and receive feedback on their progress. In one embodiment the HMD model chosen may be the i-Glasses i3pc (i3PC). The i3PC weighs 8 ounces so it should not fatigue or irritate the patient during rehabilitation exercises. It connects to a personal computer (PC) via a VGA connector and is capable of stereographic 3D.

Figure 15:
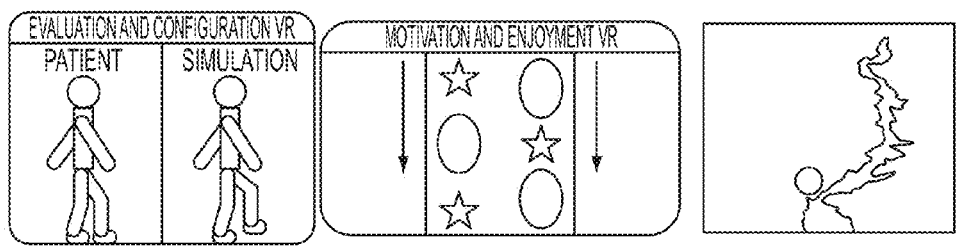
FIG. 15 shows example screens from the Virtual Reality for Calibration and Evaluation (VRCE) and Virtual Reality for Motivation and Enjoyment (VRME) displays.

For the optimum patient experience while using the ANdROS, the device will need to be calibrated for each patient. This will include collecting baseline data for the patient's current gait and assessing how much assistance the device should give the patient. The VR for Calibration and Evaluation (VRCE) interface will use the baseline data to provide feedback to the patient. The VRCE will be using known forces and angles to show a comparison of how the patient is performing compared to a simulation of the correct gait. The Virtual Reality for Motivation and Enjoyment (VRME) will be designed to be a game for the patients to experience during their rehabilitation exercises. The VRCE will be used in conjunction with the VRME as the VRME will be using the baseline values from the VRCE. The VRME will be incorporated into a rehabilitation regime that includes the use of the ANdROS. FIG. 15 shows example screens from the VRCE and VRME displays. For example, the VRME can display a series of symbols that correspond to the gait of the patient. The symbols will scroll down the screen as the patient walks. If the patient has the correct knee angles and strike positions the symbols will change from red to a normal color and the patient's score will be increased. In another example, the VRME displays for the patients a path in which they need to walk in order to collect items that will increase their score. The VRME will incorporate audio feedback to help the patients maintain their gait and cadence.

What is claimed is:

1. A lower extremity exoskeleton for gait rehabilitation comprising:
    a pelvic brace;
    an unactuated leg brace rotatably connected to the pelvic brace, further comprising:
        first upper and first lower leg shanks joined by a first rotatable knee joint to provide flexion and extension of the unactuated leg brace, wherein the first upper and first lower leg shanks are adapted to be coupled to legs of a user; and
        a sensor for measuring knee flexion and extension angles of the first rotatable knee joint;
    an actuated leg brace rotatably connected to the pelvic brace, further comprising:
        second upper and second lower leg shanks joined by a second rotatable knee joint to provide flexion and extension of the actuated leg brace, wherein the second upper and second lower leg shanks are adapted to be coupled to legs of a user; and
        means for creating a torque around the axis of rotation of the second rotatable knee joint; and
    an impedance controller for computing a desired knee angle at the first rotatable knee joint based in part on the sensor measurements and commanding a torque at the second rotatable knee joint based in part on the desired knee angle.

2. The system of claim 1 wherein the first and second upper and lower leg shanks are slotted for adjusting the distance from hip to the knee joint and from the knee joint to the ankle joint, respectively.

3. The system of claim 1 wherein the leg braces are each connected to the pelvic brace using a spherical joint that allows for flexion/extension, abduction/adduction, and rotation.

4. The system of claim 1 wherein the unactuated leg brace further comprises a sensor for measuring hip flexion and extension angles.

5. The system of claim 1 wherein the unactuated leg brace further comprises a sensor for measuring the vertical hip position.

6. The system of claim 1 wherein the unactuated leg brace further comprises a sensor for measuring ankle flexion and extension angles.

7. The system of claim 1 wherein the sensor includes a rotary potentiometer and a rotary encoder.

8. The system of claim 1 wherein each leg brace further comprises a telescopic structure that allows the exoskeleton structure to shorten during abduction.

9. The system of claim 1 further comprising a first ankle foot orthosis coupled to the unactuated leg brace and a second ankle foot orthosis coupled to the actuated leg brace.

10. The system of claim 9 wherein the first ankle foot orthosis includes a pressure transducer.

11. The system of claim 1 wherein the actuated leg brace is connected to the pelvic brace via a first hip joint that allows for flexion and extension and a second hip joint that allows for abduction and adduction; and
    wherein the unactuated leg brace is connected to the pelvic brace via a third hip joint that allows for flexion and extension and a fourth hip joint that allows for abduction and adduction.

12. The system of claim 1 further comprising a pelvic rehabilitation system for addressing secondary gait deviations.

13. The system of claim 1 wherein the impedance controller measures at least one gait related physiological parameter of the user; and estimates the cadence of the user based on at least the one gait related physiological parameter.

14. The system of claim 1 wherein the impedance controller estimates the cadence of the user; and selects a reference gait trajectory based on the estimated cadence of the user.

15. The system of claim 1 wherein the impedance controller computes a desired joint angle based on an estimated gait phase of the user and an estimated cadence of the user.

* * * * *